US010747947B2

(12) United States Patent
Narayanaswamy et al.

(10) Patent No.: US 10,747,947 B2
(45) Date of Patent: Aug. 18, 2020

(54) ELECTRONIC HEALTH RECORD COMPATIBLE DISTRIBUTED DICTATION TRANSCRIPTION SYSTEM

(71) Applicant: QSI Management, LLC, Irvine, CA (US)

(72) Inventors: Vivek Narayanaswamy, Fremont, CA (US); Alexander Stephen Karantza, Malden, MA (US); Michael Italo Cardwell, Nashville, TN (US)

(73) Assignee: NXGN Management, LLC, Irvine, CA (US)

( * ) Notice: Subject to any disclaimer, the term of this patent is extended or adjusted under 35 U.S.C. 154(b) by 415 days.

(21) Appl. No.: 15/444,266

(22) Filed: Feb. 27, 2017

(65) Prior Publication Data

US 2017/0249425 A1 Aug. 31, 2017

Related U.S. Application Data

(60) Provisional application No. 62/300,059, filed on Feb. 25, 2016.

(51) Int. Cl.

| | |
|---|---|
| G06F 40/166 | (2020.01) |
| G16H 10/60 | (2018.01) |
| G06F 21/60 | (2013.01) |
| G06F 21/62 | (2013.01) |
| G06F 9/451 | (2018.01) |
| G06F 8/658 | (2018.01) |
| G10L 15/26 | (2006.01) |
| G06F 21/78 | (2013.01) |
| G06F 19/00 | (2018.01) |
| G06F 16/13 | (2019.01) |
| G06F 21/64 | (2013.01) |

(52) U.S. Cl.
CPC .......... *G06F 40/166* (2020.01); *G06F 8/658* (2018.02); *G06F 9/451* (2018.02); *G06F 16/13* (2019.01); *G06F 19/00* (2013.01); *G06F 21/602* (2013.01); *G06F 21/6209* (2013.01); *G06F 21/64* (2013.01); *G06F 21/78* (2013.01); *G10L 15/26* (2013.01); *G16H 10/60* (2018.01); *G06F 2221/2107* (2013.01); *G06Q 2220/10* (2013.01)

(58) Field of Classification Search
CPC ....... G10L 15/26; G10L 15/265; G06Q 50/24; G06F 21/602; G06F 40/166; G16H 10/60
USPC ....... 704/235, 270, 270.1; 705/3; 369/25.01, 369/27.01
See application file for complete search history.

(56) References Cited

U.S. PATENT DOCUMENTS

| | | | | |
|---|---|---|---|---|
| 7,584,103 B2 * | 9/2009 | Fritsch | ................ | G10L 15/1815 704/257 |
| 8,086,458 B2 * | 12/2011 | Finke | .................. | G10L 15/1822 704/270 |
| 8,155,957 B1 * | 4/2012 | Takens | .................... | G10L 15/22 704/235 |

(Continued)

*Primary Examiner* — Martin Lerner
(74) *Attorney, Agent, or Firm* — Waller Lansden Dortch & Davis, LLP; Blake M. Bernard

(57) ABSTRACT

An electronic health record compatible dictation transcription system records and edits audio in an encrypted format. The system delineates audio for different electronic health record fields during dictation (i.e., recording and editing of the audio in the encrypted format), and the system inserts large predetermined text portions into transcriptions of dictated text in response to verbal prompts in the dictation audio.

13 Claims, 7 Drawing Sheets

(56) References Cited

U.S. PATENT DOCUMENTS

| | | | | |
|---|---|---|---|---|
| 8,229,742 B2* | 7/2012 | Zimmerman | G06Q 50/22 | 704/235 |
| 8,781,829 B2* | 7/2014 | Koll | G10L 15/26 | 704/235 |
| 9,305,551 B1* | 4/2016 | Johns | G10L 15/30 | |
| 2003/0046350 A1* | 3/2003 | Chintalapati | G10L 15/26 | 709/206 |
| 2004/0204938 A1* | 10/2004 | Wolfe | G10L 15/26 | 704/235 |
| 2005/0171762 A1* | 8/2005 | Ryan | G06Q 50/22 | 704/200 |
| 2007/0081428 A1* | 4/2007 | Malhotra | G16H 15/00 | 369/25.01 |
| 2009/0234643 A1* | 9/2009 | Afifi | G10L 15/26 | 704/201 |
| 2011/0054933 A1* | 3/2011 | Johnson | G06Q 50/24 | 705/3 |
| 2011/0145013 A1* | 6/2011 | McLaughlin | G06Q 50/24 | 705/3 |
| 2011/0173537 A1* | 7/2011 | Hemphill | G10L 15/26 | 715/716 |
| 2012/0303365 A1* | 11/2012 | Finke | G06Q 50/22 | 704/231 |
| 2013/0138457 A1* | 5/2013 | Ragusa | G06Q 50/24 | 705/3 |
| 2013/0238330 A1* | 9/2013 | Casella dos Santos | G10L 15/183 | 704/235 |
| 2013/0243186 A1* | 9/2013 | Poston, Jr. | G06F 3/165 | 380/28 |
| 2015/0066528 A1* | 3/2015 | Kieckens | G06F 40/40 | 705/2 |
| 2015/0371637 A1* | 12/2015 | Neubacher | G10L 15/26 | 704/235 |
| 2016/0196439 A1* | 7/2016 | Poston, Jr. | G06F 21/602 | 380/252 |

* cited by examiner

*FIG. 1*

ELECTRONIC HEALTH RECORD COMPATIBLE DISTRIBUTED DICTATION TRANSCRIPTION SYSTEM

CROSS-REFERENCES TO RELATED APPLICATIONS

This application claims priority to and hereby incorporated by reference in its entirety U.S. Provisional Patent Application Ser. No. 62/300,059 entitled "ELECTRONIC HEALTH RECORD COMPATIBLE DISTRIBUTED DICTATION TRANSCRIPTION SYSTEM" filed Feb. 25, 2016.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to dictation transcription. More particularly, this invention pertains to enabling real time dictation transcription for data entry compatible with electronic health records.

In clinical settings, patient records are dictated by a caregiver (e.g., physician) and subsequently transcribed for review of accuracy by the caregiver prior to entry in to a health record, whether that record is paper or electronic. Transcription may be partially assisted by voice recognition technology in that transcribers are provided with text derived by a computer from recorded dictation. While generally accurate, the text is manually reviewed and edited because it often contains at least a few errors. The edited text is subsequently provided back to the physician at a later time (e.g., the next day) for final review before entry in to the electronic record. This has the obvious downside of delay which, in a busy practice, can result in loss of data (e.g., the physician not recalling all aspects of the patient care and the dictated notes) and inefficiency (e.g., the physician having to sit down and take the time to recall the entire previous day).

Receiving dictation on mobile devices (e.g., cellular phones, tablets, etc.) is preferred because a physician (i.e., caregiver) can dictate notes and other relevant health record fields immediately while the information is fresh in the mind of the caregiver. However, mobile devices have somewhat limited processing power and storage capacity as compared to the servers necessary to do detailed medical record dictation transcription in reasonable amounts of time. That is, transcription must be done after dictation is completed, and storing and editing large templates in real time are generally somewhat frustrating experiences due to the limited RAM and processing speed of mobile devices.

BRIEF SUMMARY OF THE INVENTION

Aspects of the present invention provide an electronic health record compatible dictation transcription system that records and edits audio in an encrypted format. The system delineates audio for different electronic health record fields during dictation (i.e., recording and editing of the audio in the encrypted format) via selections of tags in a user interface of the recording device, and the system inserts large predetermined text portions into transcriptions of dictated text in response to verbal prompts in the dictation audio.

In one aspect, a method of transcribing audible dictation into text for entry into an electronic health record includes receiving audio at a microphone of a portable computing device. The received audio is digitized by the portable computing device. The received digitized audio is recorded in a memory of the portable computing device in an encrypted data structure. The portable computing device receives a tag selection via a user interface of the portable computing device while recording the received, digitized audio. Metadata is associated with the audio data in the encrypted file structure in response to receiving the tag selection. The associated metadata includes a timestamp in a time code. The type code corresponds to a field of the electronic health record. Speech recognition analysis is performed on the encrypted data structure to transcribe the received, digitized, and recorded audio into text. Text corresponding to audio received after the timestamp of the associated metadata is entered into the field of the electronic health record corresponding to the type code of the associated metadata.

In another aspect, a method of transcribing audible dictation into text for entry into electronic health record includes receiving audio and a microphone of a portable computing device. The audio includes a verbal macro prompt. The received audio is digitized and recorded into a memory of the portable computing device in an encrypted data structure by the portable computing device. Speech recognition analysis is performed on the encrypted data structure to transcribe the received, digitized, and recorded audio into text. Performing voice-recognition includes identifying the verbal macro prompt and replacing the verbal macro prompt with predetermined text corresponding to the verbal macro prompt. The predetermined text includes words not in the verbal macro prompt. The transcribed text is displayed on a display of the user interface of the portable computing device. The predetermined text is displayed differently from other text in the transcribed text such that a user of the portable computing device can identify and edit the predetermined text.

In another aspect, a method of editing dictated audio stored in an encrypted data structure includes receiving audio at a microphone of a portable computing device. The received audio is digitized and recorded in a memory of the portable computing device in the encrypted data structure by the portable computing device. The encrypted data structure includes a plurality of encrypted data segments and assembly data. The plurality of encrypted data segments is each representative of a portion of the received, digitized audio. The assembly data includes parameters for decrypting and assembling the plurality of encrypted data segments for playback by an audio player to render a representation of the audio received at the microphone of the portable computing device. Each segment of the plurality of segments is limited to a size cap. The portable computing device receives user input via a user interface of the portable computing device indicative of a time in the recorded audio. Replacement audio is received via the microphone of the portable computing device. The received replacement audio is for placement of the recorded audio after the time in the recorded audio indicated by the received user input indicative of the time in the recorded audio. The received replacement audio is digitized and recorded in the memory of the portable computing device in the encrypted data structure. Recording the received, digitized replacement audio includes storing an additional encrypted data segment in the plurality of encrypted data segments of the encrypted data structure without altering or deleting any of the existing encrypted data structures. Recording the received, digitized replacement audio further includes altering the assembly dated to cause the replacement audio represented by the additional encrypted data segment to be decrypted and rendered by the audio player instead of the received, digitized audio represented by at least a portion of one data segment of the plurality of data segments corresponding to the time in the recorded audio after the time indicated by the received user input.

BRIEF DESCRIPTION OF THE SEVERAL VIEWS OF THE DRAWINGS

FIG. 1 is a screen capture of an electronic health record compatible dictation transcription system user interface and a corresponding electronic health record showing tags in the dictation system mapping to fields in the electronic health record.

Reference will now be made in detail to optional embodiments of the invention, examples of which are illustrated in accompanying drawings. Whenever possible, the same reference numbers are used in the drawing and in the description referring to the same or like parts.

DETAILED DESCRIPTION OF THE INVENTION

Figure 2:
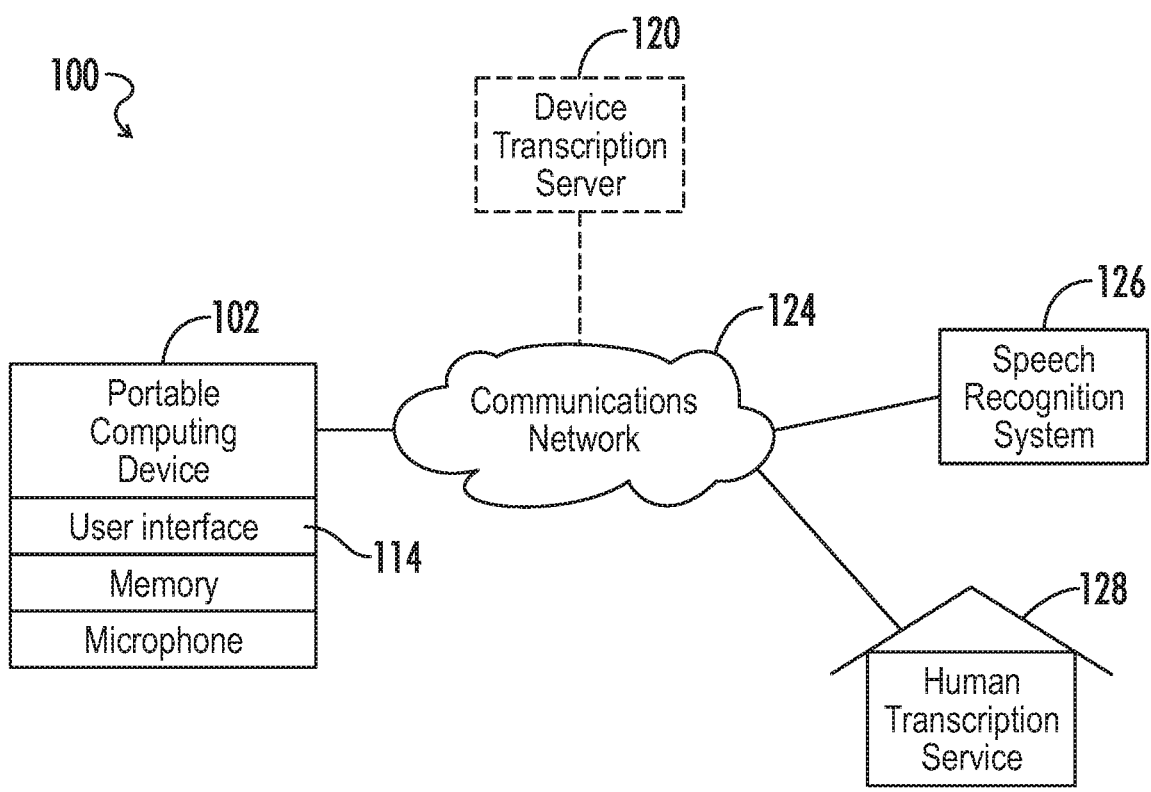
FIG. 2 is a block diagram of an electronic health record compatible dictation transcription system.
Figure 3:
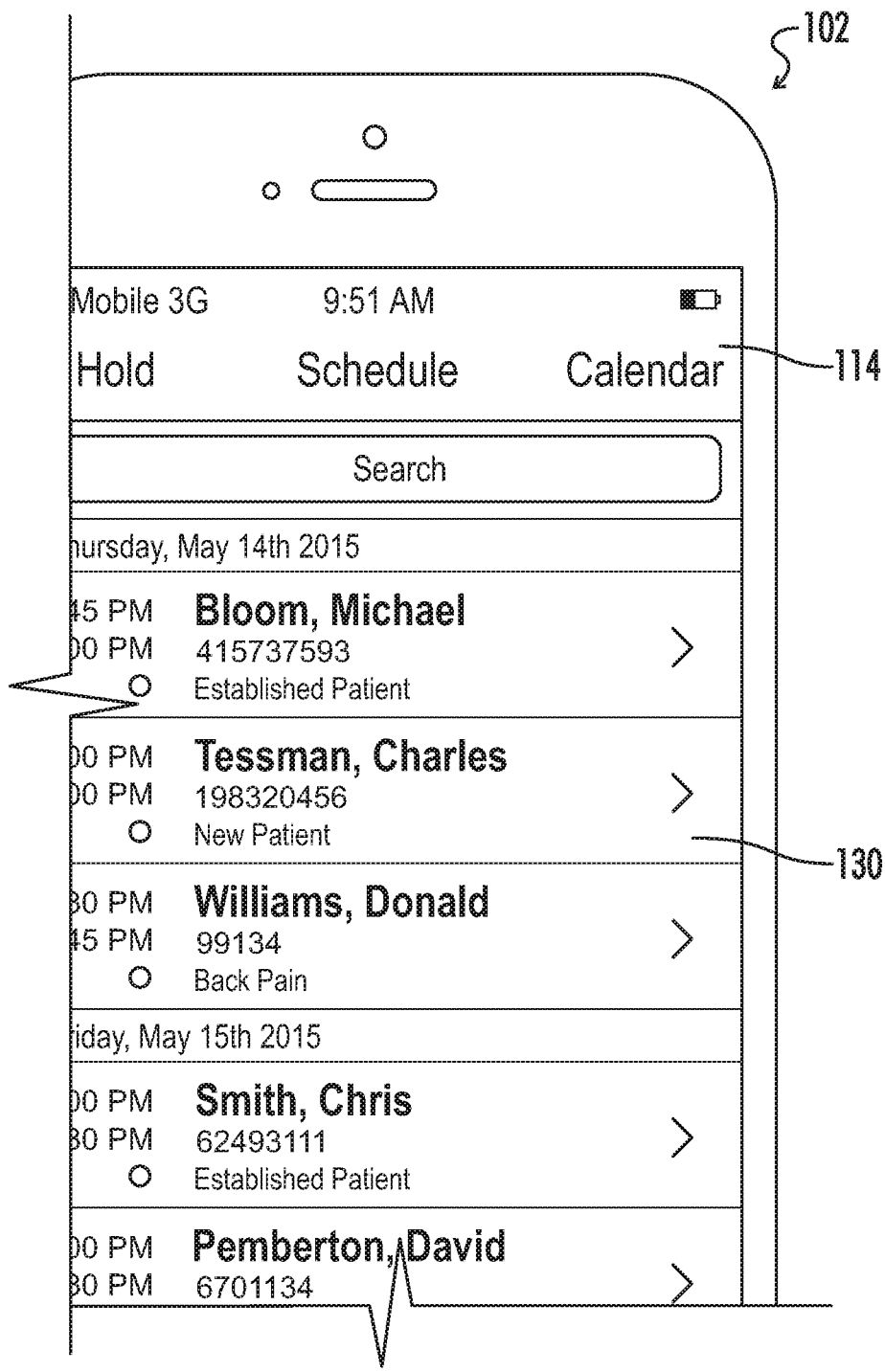
FIG. 3 is a screen capture of a user interface of a portable computing device of an electronic health record compatible dictation transcription system showing coordination of the dictation system to a scheduling system of a user of the dictation system.
Figure 4:
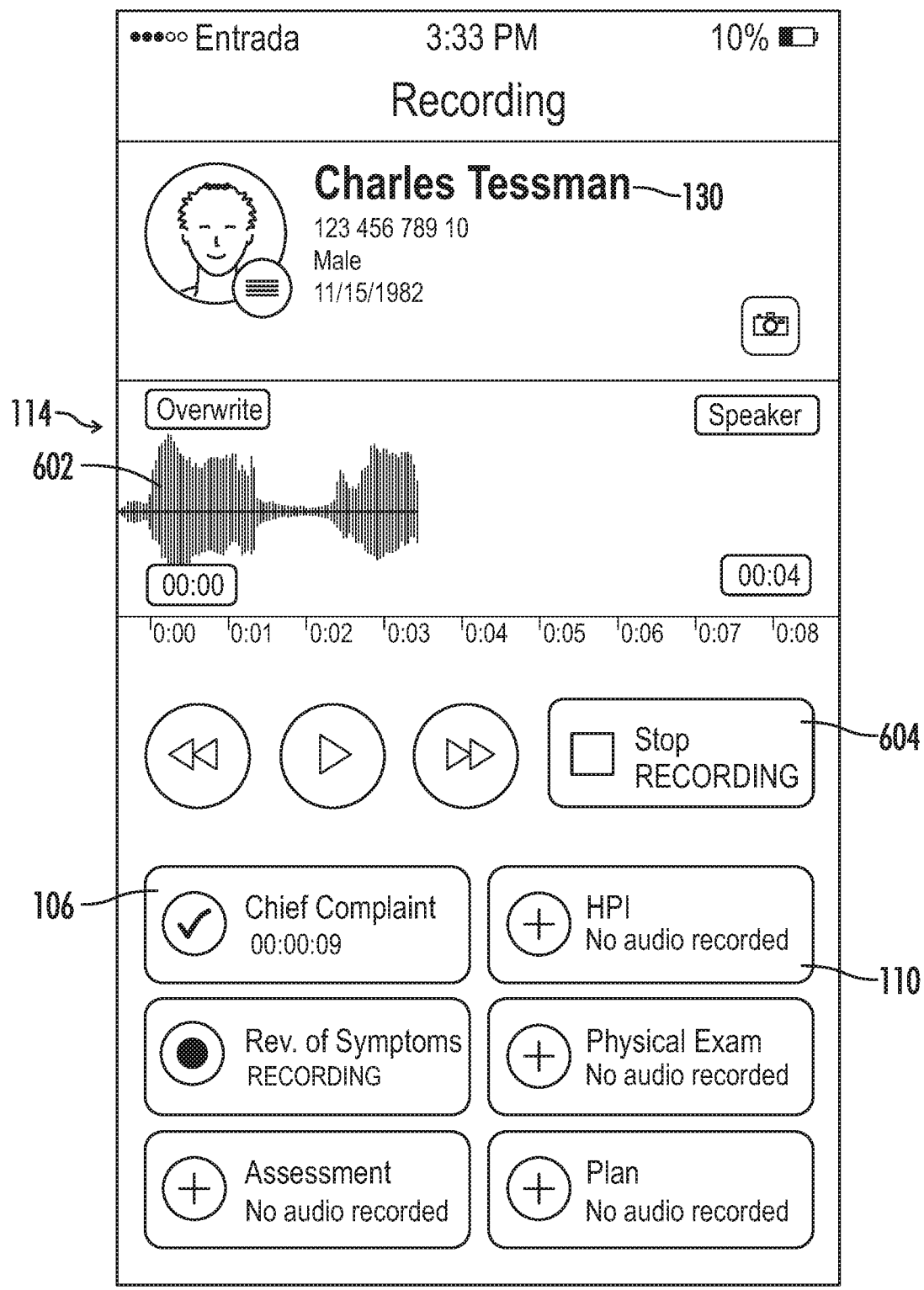
FIG. 4 is a screen capture of a user interface of a portable computing device of an electronic health record compatible dictation transcription system showing controls for recording, tagging, playing back, and editing audio stored in an encrypted data structure.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of the embodiments described herein, a number of terms are defined below. The terms defined herein have meanings as commonly understood by a person of ordinary skill in the areas relevant to the present invention. Terms such as "a," "an," and "the" are not intended to refer to only a singular entity, but rather include the general class of which a specific example may be used for illustration. The terminology herein is used to describe specific embodiments of the invention, but their usage does not delimit the invention, except as set forth in the claims.

The phrase "in one embodiment," as used herein does not necessarily refer to the same embodiment, although it may. Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Terms such as "providing," "processing," "supplying," "determining," "calculating" or the like may refer at least to an action of a computer system, computer program, signal processor, logic or alternative analog or digital electronic device that may be transformative of signals represented as physical quantities, whether automatically or manually initiated.

Figure 1:
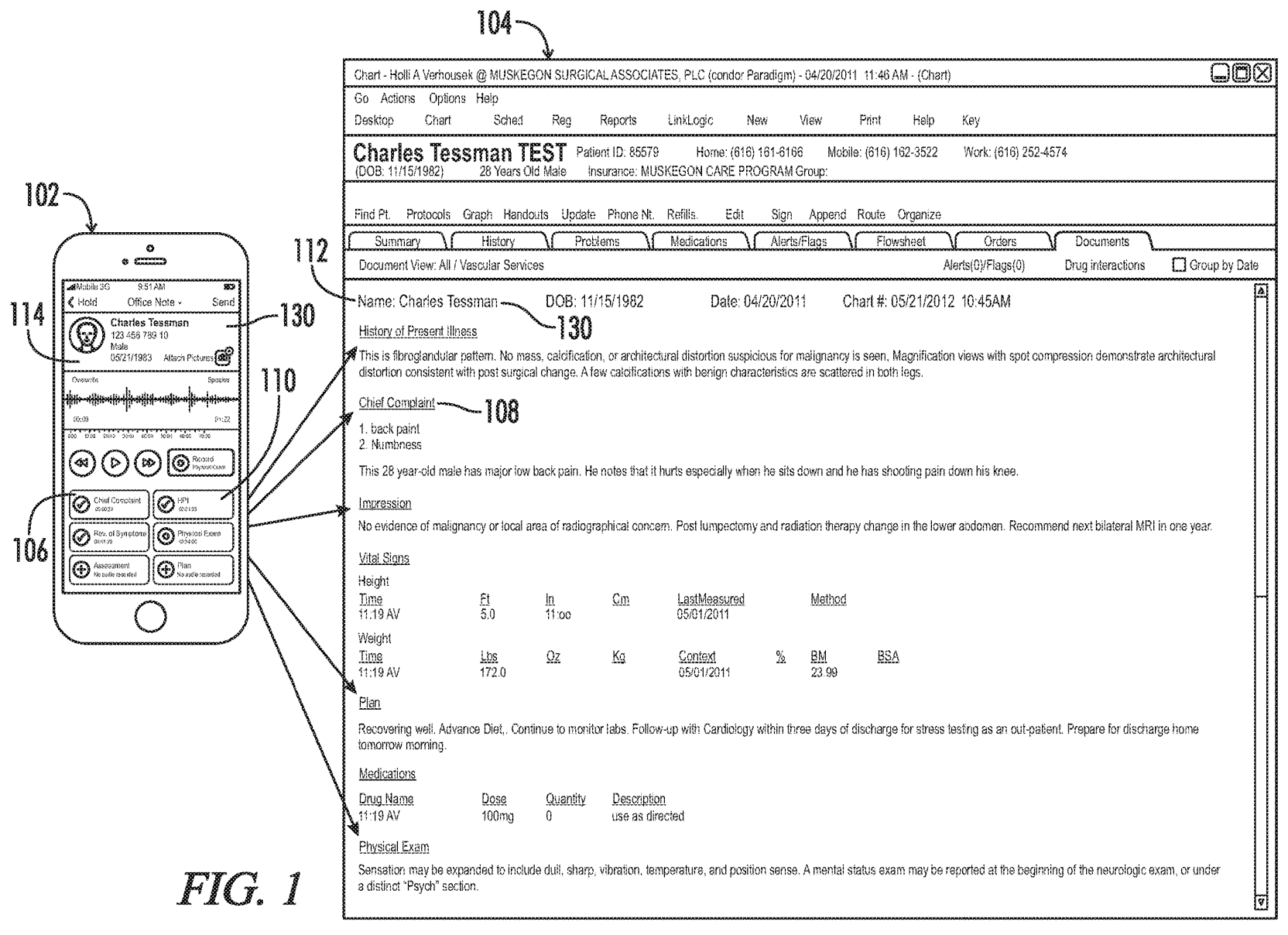

Referring to FIGS. 1-7, a method of transcribing audible dictation into text for entry into electronic health record 104 includes receiving audio at a microphone of a portable computing device 102. The portable computing device 102 digitizes the received audio. The portable computing device 102 records the received, digitized audio into a memory of the portable computing device 102 in an encrypted data structure. In one embodiment, the recording process is initiated by selecting a patient 130 from a list of patients via the user interface 114 of the portable computing device 102 (see FIG. 3). In one embodiment, actual recording of the audio begins with selection of a tag displayed in the user interface 114 of the portable computing device 102. In one embodiment, the selection and arrangement of tags displayed in the user interface 114 of the portable computing device 102 can be altered by the user. As the user operates the portable computing device 102 to record audio, a waveform 602 is shown in the user interface 114 (see FIG. 4). The user may stop recording (i.e., pause) for a selected tag via a stop recording button 604 of the user interface 114, or by selecting another tag. If the user selects a tag for which audio has already been recorded, recording is not automatically started. The user may use the waveform 602 to select a point in the corresponding audio at which to begin recording. In one embodiment, a tag that already has associated audio may be held down (i.e., pressed on upon by the user for an extended period of time) to bring up a contextual menu including insert, overwrite, delete to end, delete all, and recorded digital audio. In the same way, the user may select a point in the waveform 602 at which to begin recording, and if the user presses on that point in the waveform 602 for an extended period of time, contextual menu comes up including options to insert, overwrite, or delete to end (i.e., of the audio associate with the selected tag).

The method of transcribing audible dictation into text continues with a user interface 114 of the portable computing device 102 receiving a tag selection 110 (i.e., the user selects a tag 110) while recording the received, digitized audio. The computing device 102 associates metadata with the audio data in the encrypted file structure in response to receiving the tag selection 110. The associated metadata includes a timestamp and a type code. The type code corresponds to a field 112 of the electronic health record 104. Speech recognition analysis is performed on the encrypted data structure to transcribe the received, digitized, and recorded audio into text. Text corresponding to audio received after the timestamp of the associated metadata is entered into the field 112 of the electronic health record 104 corresponding to the type code of the associated metadata. The type code corresponds to the selected tag 110 of the tag selection.

In one embodiment, the tag selection 110 is a second tag selection. The portable computing device 102 is configured to begin digitizing and recording the received audio in response to receiving a first tag selection 106 via the user interface 114 of the portable computing device 102. A type code corresponding to a first selected tag 106 of the first tag selection is different from the type code corresponding to the second selected tag 110 of the second tag selection.

In one embodiment, as shown in FIG. 2, performing speech recognition analysis on the encrypted data structure includes transmitting the encrypted data structure and associated metadata from the portable computing device 102 to a speech recognition system 126 via a communications network 124. A text transcript is then received from the speech recognition system 126 via the communications network 124 at the portable computing device 102, and the text transcript has a plurality of text segments, each takes segment corresponding to a type code of a plurality of type codes. In one embodiment, the type code of each text segment corresponds to a tag displayed in the user interface 114 of the portable computing device 102. In one embodiment, the user may opt for manual transcription of the audio data. In this embodiment, the audio data is routed by the speech recognition system 126 to a human transcription service 128 via the communications network 124, and the transcript returns to the portable computing device 102 via the same pathway.

Figure 5:
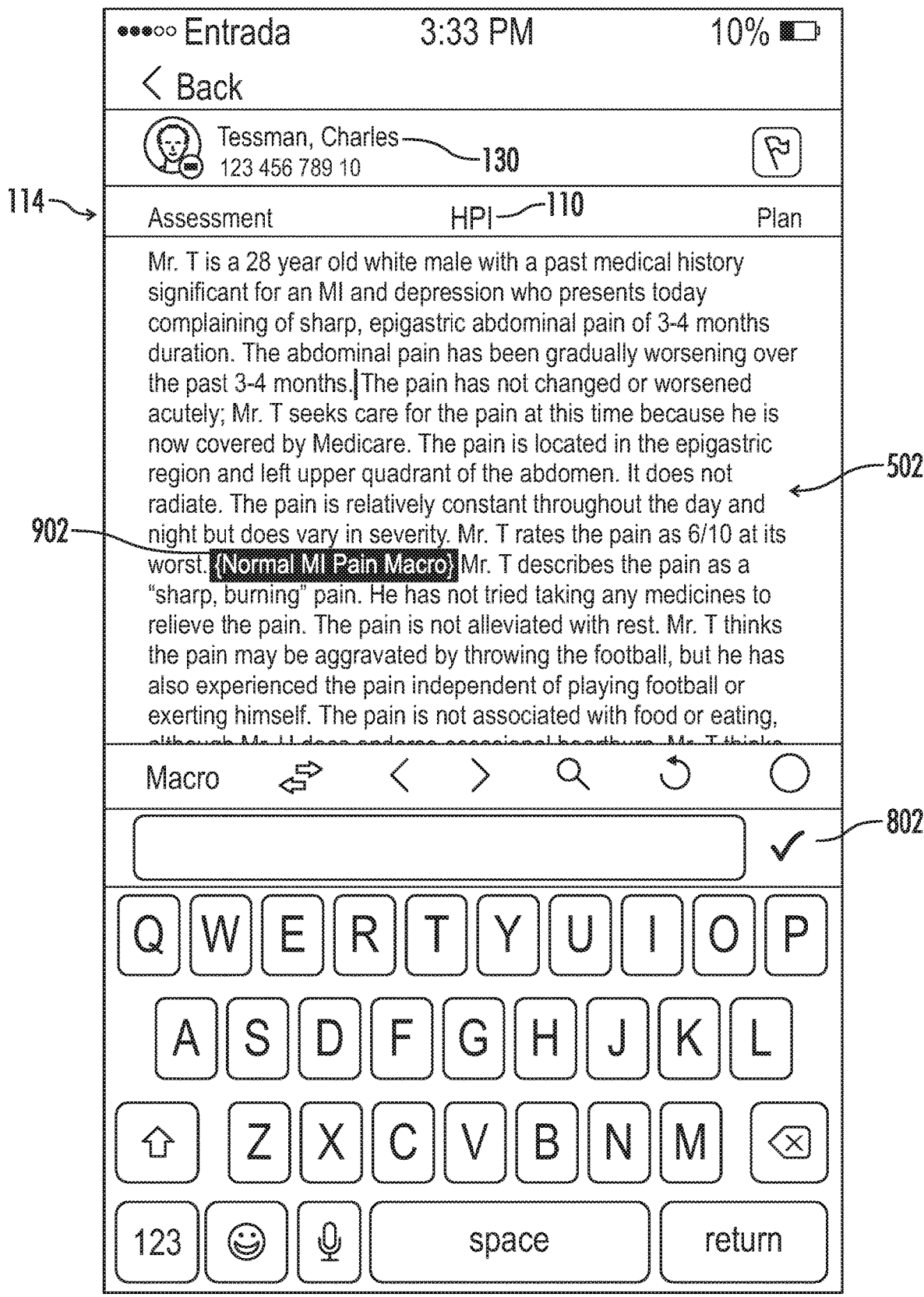
FIG. 5 is a screen capture of a user interface of a portable computing device of an electronic health record compatible dictation transcription system showing a system for editing and approving a transcript including a macro.
Figure 6:
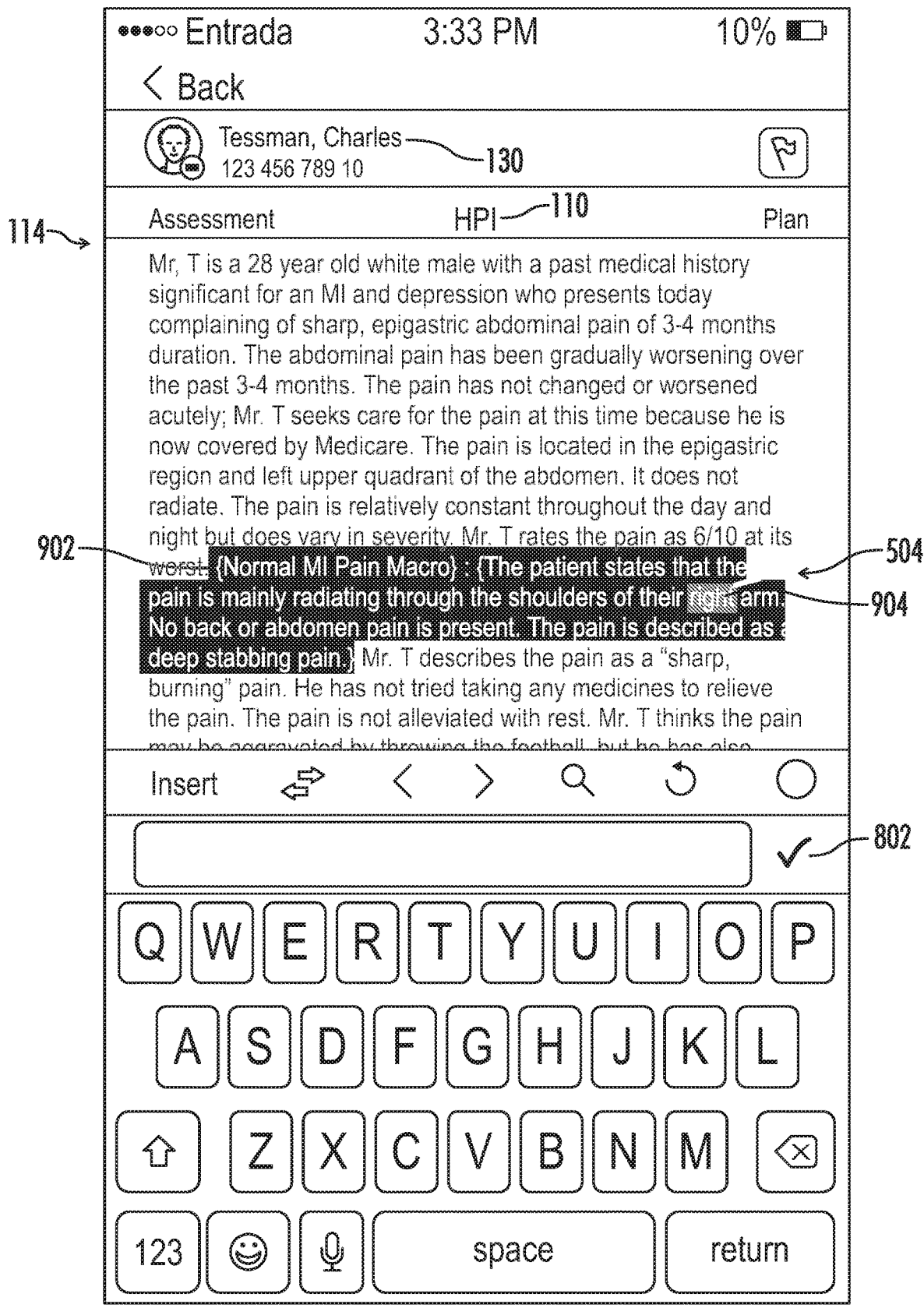
FIG. 6 is a screen capture of the user interface of the portable computing device of the electronic health record compatible dictation transcription system of FIG. 5 showing expansion of the visual representation of the macro into predetermined corresponding text.
Figure 7:
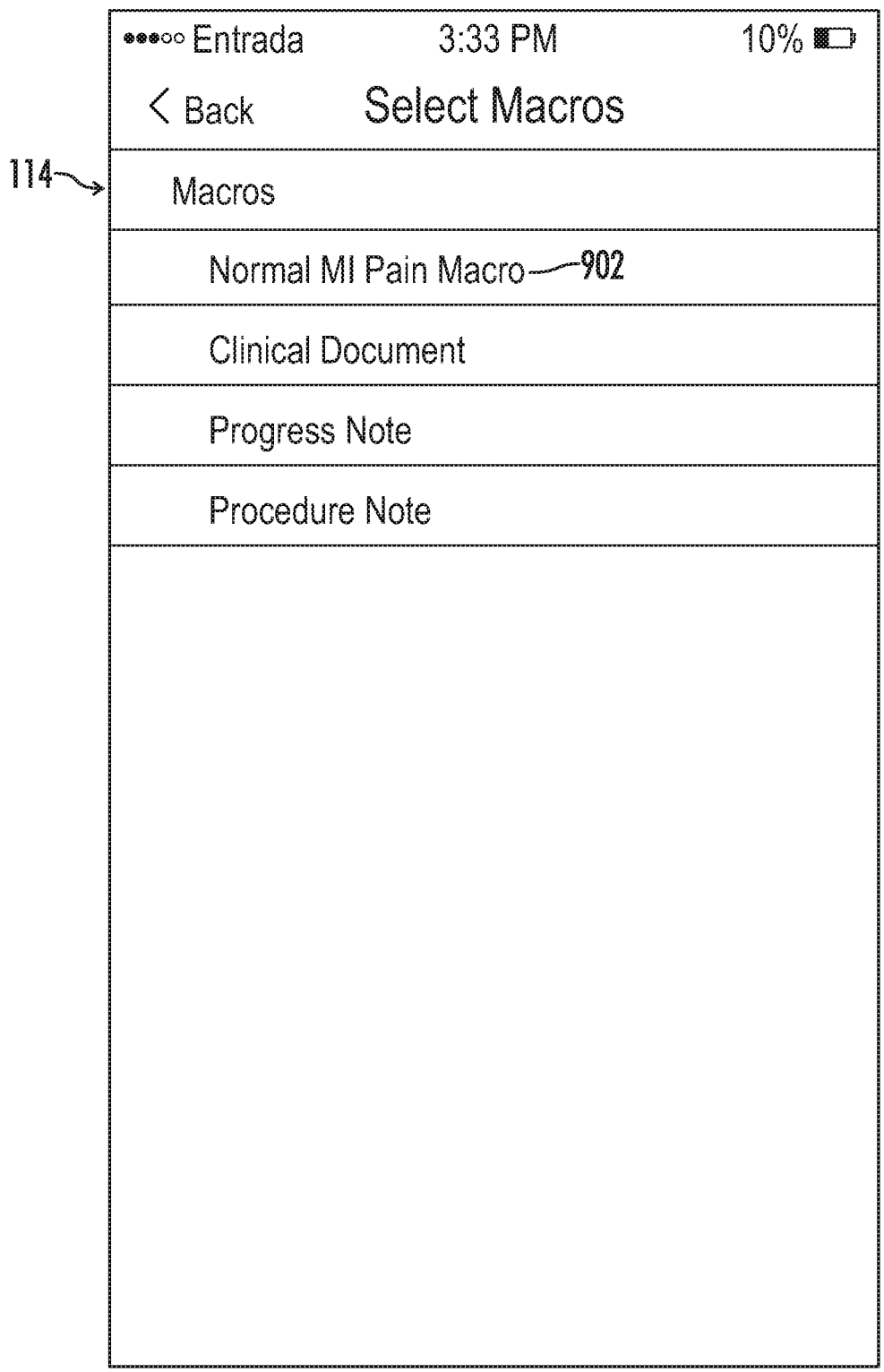
FIG. 7 is a screen capture of the user interface of the portable computing device of the electronic health record compatible dictation transcription system of FIG. 5 showing selection of a macro for inserting into the displayed text.

In one embodiment, entering text in the electronic health record 104 includes displaying via the user interface 114 of the portable computing device 102 a text segment 502 of a text transcript of the encrypted data structure transcribed into text (see FIGS. 5-7). The text segment corresponds to the audio received after the timestamp of the associated metadata. Entering text in the electronic health record 104 further includes receiving edits to the displayed text 502 via the user interface 114 of the portable computing device 102, and editing the displayed text 504 as a function of the received edits. Entering text in the electronic health record 104 further includes receiving approval of the displayed, edit text 504 via the user interface 114 and storing the edited text segment 504 in the electronic health record 104 in the field of the electronic health record 104 corresponding to the type code of the metadata associated with the audio corresponding to the text segment 502, 504.

In one embodiment, storing the edited text segment 504 includes transmitting, via the communications network 124, the edited text 504 and associated metadata including the associated type code and a patient identifier 130 (e.g., patient number or patient name) from the portable computing device 102 to an electronic health record database 104. Said storing further comprises storing the transmitted, edited text 504 in the electronic health record 104 in a patient record associated with the transmitted patient identifier 130 and in the field 112 of the electronic health record 104 corresponding to the transmitted type code.

In one embodiment, a user approves text as displayed 504 by selecting an approve button 802 of the user interface 114. The portable computing device 102 thus receives approval of the displayed text. In one embodiment, in response to receiving approval of the displayed text, the portable computing device 102 displays a second text segment of the text transcript of the encrypted data structure transcribed into text, said second text segment corresponding to audio received after a timestamp of the associated metadata corresponding to the second tag selection 110. The user interface 114 separately receives approval of the displayed text of the second text segment via the user interface 114 (i.e., separate from approval of the displayed text corresponding to the first tag selection 106). The portable computing device 102 then stores each text segment in the corresponding field of the electronic health record 104. In one embodiment, the portable computing device 102 stores the first text segment in the corresponding field of the electronic health record 104 upon receiving approval of the displayed text corresponding to the first tag selection 106, and subsequently stores the second text segment in the corresponding field of the electronic health record 104 upon receiving approval of the displayed text corresponding to the second tag selection 110. In one embodiment, when the user interface 114 is displaying text corresponding to the first tag selection 106, and the user interface 114 receives second tag selection 110, the user interface 114 displays a second text segment of the text transcript corresponding to audio received after timestamp of the associated metadata corresponding to the second tag 110 of the second test selection. In this embodiment, when the user provides approval via the approve button 802 of any text segment, each and every text segment of the text transcript of the encrypted data structure transcribed into text is entered or stored in the corresponding field of the electronic health record 104.

It is contemplated within the scope of the claims that a device transcription server 120 may be employed in cooperation with the portable computing device 102. That is, as used herein, transmitting data to the portable computing device 102 may include transmitting data to the device transcription server 120, making the transmitted data available to the portable computing device 120, and subsequently loading the transmitted data to the portable computing device 102 at the request of the portable computing device 102 (e.g., when the user selects a transcription from a list of available transcriptions). In this embodiment, the device transcription server 120 would function similar to Microsoft exchange server, and the portable computing device would function as an email client (e.g., Microsoft Outlook). Additionally, the device transcription server 120 function may be incorporated into the speech recognition system 126. Further, the electronic health record 104 housed in the electronic health record database 104 may be incorporated into the speech recognition system 126, the device transcription server 120, or some third party database (e.g., the provider of the electronic health record service) without deviating from the scope of the claims.

In one embodiment, a method of transcribing audible dictation into text for entry into electronic health record 104 includes receiving audio at the microphone of the portable computing device 102, wherein the audio includes a verbal macro prompt. The portable computing device 102 digitizes the received audio, and records the received, digitized audio in a memory of the portable computing device 102 in an encrypted data structure. The method includes performing speech recognition analysis on the encrypted data structure to transcribe the received, digitized, and recorded audio into text. Performing voice recognition includes identifying the verbal macro prompt and replacing the verbal macro prompt with predetermined text corresponding to the verbal macro prompt. The predetermined text includes words not in the verbal macro prompt. The transcribed text is displayed on a display of the user interface 114 of the portable computing device 102. The predetermined text 902 is displayed differently from other text in the transcribed text such that the user of the portable computing device 102 can identify and edit the predetermined text. In one embodiment, only a portion 904 of the predetermined text is displayed differently from the other text of the transcribed text. This may be useful for example, when templates including options such as "left" or "right" are the predetermined text. The predetermined text would be displayed with a default option 904 highlighted (or otherwise discolored). In one embodiment, displaying the predetermined text differently from other text in the transcribed text includes displaying the macro name 902 corresponding to the verbal macro prompt wherein the macro name is displayed differently from the other text in the transcribed text. When the user selects the macro name 902 via the user interface 114 of the portable computing device 102, and in response to receiving said input, the portable computing device expands the macro by either replacing the macro name 902 with the predetermined text or appending additional predetermined text after the macro name 902.

In one embodiment, a method of editing dictated audio stored in an encrypted data structure includes receiving audio at the microphone of the portable computing device 102, digitizing the received audio, and recording the received, digitized audio in the memory of the portable computing device 102 in the encrypted data structure. The encrypted data structure includes a plurality of encrypted data segments, each representative of a portion of the received, digitized audio, and assembly data. The assembly data includes parameters for decrypting and assembling the plurality of encrypted data segments for playback by an audio player to render representation of audio received at the microphone of the portable computing device. Each segment of the plurality of segments is limited to a size cap. In this method, user input received via the user interface 114 of the portable computing devices is indicative of a time in the recorded audio. The portable computing device 102 then receives replacement audio via the microphone of the portable computing device 102 wherein the received replacement audio is for placement of the recorded audio after the time the recorded audio indicated by the received user input indicative of the time the recorded audio. Portable computing device 102 digitizes the received replacement audio, and records the received, digitized replacement audio in the memory of the portable computing device 102 in the encrypted data structure. Recording the received, digitized replacement audio includes storing an additional encrypted data segment in the plurality of encrypted data segments of the encrypted data structure without altering or deleting any of the existing encrypted data segments. Recording further includes altering the assembly data to cause the replacement audio represented by the additional encrypted data segment to be decrypted and rendered by the audio player instead of the received, digitized audio represented by at least a portion of one data segment of the plurality of data segments corresponding to the time in the recorded audio after the time indicated by the received user input.

In one embodiment, a system 100 for transcribing audible dictation into text for entry into an electronic health record 104 includes a user interface 114 for tag selection. During dictation, when a user of the system 100 selects a tag button 106 displayed on the user interface 114, the system 100 inserts metadata into an audio file corresponding to the dictation. The metadata includes a timestamp and a type code. The dictation system 100 associates audio following the selection of the tag button 106 into the electronic health record in a field of the electronic health record 104 corresponding to the type code.

In another embodiment, a system 100 for editing dictated audio stores the audio in an encrypted file structure. The encrypted file structure includes a plurality of data segments, each encrypted, and assembly data for decrypting and ordering the data segments to reconstitute (i.e., render) the original dictated audio. Instead of simultaneously decrypting, assembling, and rendering audio data while recording, encoding and overwriting the audio data, the replacement audio is inserted. The replacement audio is recorded in a new data segment, and the assembly data of the encrypted file structure is altered to play (i.e., decrypt, assemble, and render) the replacement data segment instead of at least a portion of at least one of the plurality of data segments.

In yet another embodiment, audio dictated to a medical transcription system 100 includes at least one verbal macro prompt. After the audio is recorded, it is analyzed by the portable computing device it is recorded on 102, or sent to a server for voice recognition 126. During the voice recognition transcription, the system 100 identifies the verbal macro prompt and replaces the corresponding text with predetermined macro text (see FIGS. 5 and 6). When the transcribed text is displayed to a user of the portable computing device 102, the macro text, or at least a portion thereof is displayed differently from the rest of the transcription text to call the user's attention to the text. The user edits the macro text and approves the transcription via the user interface 114 of the portable computing device 102, and the transcribed text is entered into an electronic medical record 104. For example, during the recording process, the user may say "Insert Normal MI Pain" which is the name of a macro or a verbal macro prompt. The user clicks send upon completion of dictation and the recorded file (i.e., encrypted data structure) then gets sent off to a speech recognition server 126 via a communications network 124. If the user chooses to edit on the device 102, the draft speech transcribed text will display on the device 102. However, before the transcribed text comes back to the device 102, the speech (i.e., voice) recognition server 126 identifies "Insert Normal MI Pain" or other titles of macros and maps them to an appropriate macro. The user will see that the recording has returned to the portable computing device 102 (or to a device transcription server 120 storing the transcriptions for download by the portable computing device 102) and clicks on a representation of the transcribed text to view the draft. In the draft text, along with all of the other dictation, it will say "Normal MI Pain Macro" which will be a different color or otherwise indicated that this text is different from the other text to indicate that it is a macro (i.e., predetermined text inserted via a macro). The user can then expand, change, delete or edit the predetermined text of the macro returned in the transcription. The user can also insert a macro that was not identified in the speech recognition or that they forgot to dictate by tapping a point in the displayed text for insertion and subsequently selecting a macro via the user interface 114 (see FIG. 7) for insertion at the selected insertion point.

It will be understood by those of skill in the art that navigating between user interface views is accomplished by selecting a tab or object in a current user interface view corresponding to another user interface view, and in response to selecting the tab or object, the user interface updates with said another user interface view corresponding to the selected tab or object. See Appendix 1 and Appendix 2 for the navigational results of selecting different items in the user interface views shown in FIGS. 3-7.

It will be understood by those of skill in the art that providing data to the system or the user interface may be accomplished by clicking (via a mouse or touchpad) on a particular object or area of an object displayed by the user interface, or by touching the displayed object in the case of a touchscreen implementation.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. Although embodiments of the present invention have been described in detail, it will be understood by those skilled in the art that various modifications can be made therein without departing from the spirit and scope of the invention as set forth in the appended claims.

A controller, processor, computing device, client computing device or computer, such as described herein, includes at least one or more processors or processing units and a system memory. The controller may also include at least some form of computer readable media. By way of example and not limitation, computer readable media may include computer storage media and communication media. Computer readable storage media may include volatile and nonvolatile, removable and non-removable media implemented in any method or technology that enables storage of information, such as computer readable instructions, data structures, program modules, or other data. Communication media may embody computer readable instructions, data structures, program modules, or other data in a modulated data signal such as a carrier wave or other transport mechanism and include any information delivery media. Those skilled in the art should be familiar with the modulated data signal, which has one or more of its characteristics set or changed in such a manner as to encode information in the signal. Combinations of any of the above are also included within the scope of computer readable media. As used herein, server is not intended to refer to a single computer or computing device. In implementation, a server will generally include an edge server, a plurality of data servers, a storage database (e.g., a large scale RAID array), and various networking components. It is contemplated that these devices or functions may also be implemented in virtual machines and spread across multiple physical computing devices.

This written description uses examples to disclose the invention and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Thus, although there have been described particular embodiments of the present invention of a new and useful ELECTRONIC HEALTH RECORD COMPATIBLE DISTRIBUTED DICTATION TRANSCRIPTION SYSTEM it is not intended that such references be construed as limitations upon the scope of this invention except as set forth in the following claims.

What is claimed is:

1. A method of transcribing audible dictation into text for entry into an electronic health record, said method comprising:
    receiving audio at a microphone of a portable computing device;
    digitizing the received audio;
    recording the received, digitized audio in a memory of the portable computing device in an encrypted data structure;
    receiving a tag selection via a user interface of the portable computing device while recording the received, digitized audio;

associating a first set of metadata with the audio data in the encrypted data structure in response to receiving the tag selection, wherein:
   the associated metadata comprises a timestamp and a type code; and
   the type code corresponds to a field of the electronic health record;
receiving a second tag selection via a user interface of the portable computing device while recording the received, digitized audio;
associating a second set of metadata with the audio data in the encrypted file structure in response to receiving the second tag selection, wherein:
   the associated metadata comprises a second timestamp and a second type code; and
   the second type code corresponds to a second field of the electronic health record;
   performing speech recognition analysis on the encrypted data structure to transcribe the received, digitized, and recorded audio into a text transcript including a first text segment corresponding to audio received after the timestamp of the tag selection and a second text segment corresponding to audio received after the second timestamp of the second tag selection;
receiving approval of the entire text transcript; and
entering the text transcript into the electronic health record upon receiving approval of the text transcript by entering the first text segment into a first field of the electronic health record corresponding to the type code, and entering the second text segment into a second field of the electronic health record corresponding to the second type code.

2. The method of claim 1, wherein:
the type code corresponds to the selected tag of the tag selection.

3. The method of claim 1, wherein:
the portable computing device is configured to begin digitizing and recording the received audio in response to receiving the tag selection via the user interface of the portable computing device; and
a type code corresponding to the selected tag of the tag selection is different from the second type code corresponding to a second selected tag of the second tag selection.

4. The method of claim 1, wherein:
performing speech recognition analysis on the encrypted data structure comprises:
   transmitting the encrypted data structure and associated metadata to a speech recognition system via a communications network.

5. The method of claim 1, wherein:
entering text in the electronic health record comprises:
   displaying, via a user interface of the portable computing device, one or more of the first or second text segments of the text transcript of the encrypted data structure transcribed into text;
   receiving edits to the displayed text via the user interface of the portable computing device for at least one of the text segments;
   editing the displayed text as a function of the received edits;
   receiving approval of the displayed, edited text via the user interface; and
   storing the edited text segment in the electronic health record in the corresponding field of the electronic health record corresponding to the type code of the metadata associated with the audio corresponding to the edited text segment.

6. The method of claim 5, wherein:
storing the edited text segment comprises:
   transmitting, via a communications network, the edited text and the corresponding associated metadata comprising the corresponding associated type code and a patient identifier from the portable computing device to an electronic health record database storing the electronic health record; and
   storing the transmitted, edited text segment in the electronic health record in a patient record associated with the transmitted patient identifier and in the field of the electronic health record corresponding to the transmitted type code.

7. The method of claim 1, wherein:
entering text in the electronic health record comprises:
   displaying, via a user interface of the portable computing device, a first text segment of the text transcript of the encrypted data structure transcribed into text;
   receiving edits to the first text segment of the displayed text via the user interface of the portable computing device;
   editing the displayed text as a function of the received edits;
   receiving approval of the displayed, edited text via the user interface;
   in response to receiving approval of the displayed, edited text via the user interface, displaying the second text segment of the text transcript of the encrypted data structure transcribed into text, wherein the tag selection is a first tag selection and the second tag selection corresponds to a second tag different from a first tag of the first tag selection;
   receiving approval of the displayed text of the second text segment;
   storing the edited text segment in the electronic health record in the field of the electronic health record corresponding to the type code of the metadata associated with the audio corresponding to the first text segment; and
   storing the second text segment in the electronic health record in the field of the electronic health record corresponding to a type code of the metadata associated with the audio corresponding to the second text segment.

8. The method of claim 7, wherein:
the edited text segment is stored in the electronic health record in response to receiving approval of the displayed, edited text via the user interface of the portable computing device; and
the second text segment is stored in the electronic health record in response to receiving approval of the displayed text of the second text segment.

9. The method of claim 1, wherein:
entering text in the electronic health record comprises:
   displaying, via a user interface of the portable computing device, the first text segment of a text transcript of the encrypted data structure transcribed into text, wherein the tag selection is a first tag selection of a first tag;
   receiving edits to the displayed text via the user interface of the portable computing device;
   editing the displayed text as a function of the received edits;

receiving the second tag selection via the user interface of the portable computing device while displaying the text segment of the text transcript;

displaying the second text segment of the text transcript of the encrypted data structure transcribed into text, said second text segment corresponding to audio received after the second time stamp of the associated metadata corresponding to a second tag of the second tag selection, wherein the second tag selection corresponds to a second tag different from the first tag of the first tag selection;

receiving approval of the displayed text of the second text segment; and storing the second text segment in the electronic health record in the field of the electronic health record corresponding to a type code of the metadata associated with the audio corresponding to the second text segment.

10. The method of claim 9, wherein:

entering text in the electronic health record further comprises:

storing the edited text segment in the electronic health record in the field of the electronic health record corresponding to the type code of the metadata associated with the audio corresponding to the text segment; and wherein:

receiving approval of the displayed text of the second text segment is interpreted as also receiving approval of the displayed, edited text via the user interface such that the edited text segment is caused to be stored in the electronic health record in the field of the electronic health record corresponding to the type code of the metadata associated with the audio corresponding to the first text segment.

11. The method of claim 1, wherein:

performing speech recognition analysis on the encrypted data structure comprises:

transmitting the encrypted data structure and associated metadata to a speech recognition system via a communications network; and receiving the text transcript from the speech recognition system via the communications network at the portable computing device, wherein the text transcript has a plurality of text segments, each text segment corresponding to a type code of a plurality of type codes, wherein:

receiving the text transcript at the portable communications device comprises receiving the text transcript at a device transcription server associated with the portable computing device, and retrieving the text transcript from the device transcription server to the portable computing device.

12. The method of claim 1, wherein:

performing speech recognition analysis on the encrypted data structure comprises:

transmitting the encrypted data structure and associated metadata to a speech recognition system via a communications network; and receiving the text transcript from the speech recognition system via the communications network at the portable computing device, wherein the text transcript has a plurality of text segments, each text segment corresponding to a type code of a plurality of type codes, wherein:

receiving the text transcript at the portable communications device comprises making the text transcript available for retrieval from the speech recognition system by the portable computing device, and retrieving the text transcript from the speech recognition system to the portable computing device.

13. The method of claim 1, wherein:

the audio includes a verbal macro prompt; and said performing speech recognition analysis on the audio further comprises:

identifying the verbal macro prompt; and replacing the verbal macro prompt with predetermined text corresponding to the verbal macro prompt, wherein the predetermined text comprises words not in the verbal macro prompt.

* * * * *